United States Patent [19]
Goodman

[11] Patent Number: 5,178,541
[45] Date of Patent: Jan. 12, 1993

[54] METHOD FOR NEUTRALIZING MERCURY DERIVED FROM DENTAL AMALGAMS

[76] Inventor: Ramgopal D. Goodman, 58539 Charles St., Martin Ferry, Ohio 43935

[21] Appl. No.: 806,228

[22] Filed: Dec. 13, 1991

[51] Int. Cl.$^5$ .............................................. A61C 5/04
[52] U.S. Cl. ..................................... 433/226; 433/228.1
[58] Field of Search ....................... 433/215, 226, 228.1

[56] References Cited

U.S. PATENT DOCUMENTS

| | | | |
|---|---|---|---|
| 1,379,744 | 5/1921 | Congreve | 429/49 |
| 3,018,778 | 1/1962 | Brilliant | 433/226 |
| 4,354,942 | 10/1982 | Kaczur et al. | 210/751 |
| 4,844,815 | 7/1989 | Ader et al. | 210/914 |
| 4,914,135 | 4/1990 | Herschler | 514/711 |

Primary Examiner—John J. Wilson
Attorney, Agent, or Firm—Richard C. Litman

[57] ABSTRACT

A method for preventing mercury released from amalgam dental fillings from passing into and adversely effecting the body by the use of sulfur in effective amounts. A protective layer may be formed over hardened amalgam surfaces by brushing a tooth surface with a toothpaste composition containing sulfur. Alternatively, surfaces of a tooth cavity can be coated with a lining composition containing sulfur, and the dental amalgam may then inserted into the lined cavity to form dental restorations of improved corrosion resistance. Also, sulfur may be incorporated into setting compositions comprising a dental amalgam alloy composed mainly of silver and tin, and including mercury in an amount sufficient to amalgamate said alloy.

6 Claims, No Drawings

METHOD FOR NEUTRALIZING MERCURY DERIVED FROM DENTAL AMALGAMS

BACKGROUND OF THE INVENTION

1. Field of the Invention

The present invention relates to a method for neutralizing mercury derived from dental amalgams. More particularly, the invention pertains to the use of sulfur for inhibiting the harmful effects of mercury caused by the leaching of mercury from amalgam fillings.

2. Description of the Prior Art

Amalgams or alloys of metal powders composed mainly of silver and mercury have long been used as dental filling materials. Dental amalgams as hardenable mixtures are prepared by triturating or mixing silver based alloys with liquid mercury. These initially pliable mixtures are filled into teeth cavities where they set to a hard mass after a time at mouth temperatures by an amalgamation reaction between the mercury and silver or other metal components. Due to the fact that such amalgams yield strengths durable to occlusal pressures, have good workability in preparation, and have an external configuration consistent with the remainder of the tooth, they have been commercialized for dental restorations up to the present.

However, recent studies show that dental amalgams do not have the characteristic durability and permanence that earlier distinguished these filling materials. It has now been found that conventional dental amalgams have a thermal expansion significantly different than that of the tooth. Consequently, when hot and cold foods or liquids come in contact with the restored tooth, the differences in expansion and contraction between the tooth structure and the amalgam cause mercury leakage around the margin of the fillings examined.

It was also found that mercury is released from silver-tin amalgam restorations by such factors as differential aeration. Differential aeration is a common oxidative phenomenon that causes corrosion or tin dissolution to occur in areas at the restoration-tooth interface. Over a period of time, the tin dissolves or corrodes because tin is less noble and therefore more easily oxidized than either Ag or Hg. The net effect is that the oxidation of tin atoms results in tin ions within the interface. This reduces the strength of the amalgam restoration and contributes to partial extrusion of the restoration from the cavity. In addition, the presence of tin ions in the area adjacent to the cavity surfaces promotes ionization of mercury which substantially increases the tendency for the mercury to vaporize subsequent to leaching from the amalgam restorations.

It is well known that mercury is essentially a harmful substance to which severe environmental standards are applied. The maximum permitted mercury content of air is 0.05 mg/m$^3$. Mercury vapor is colorless and odorless and therefore difficult to detect. The toxic effect of its inhaled vapors has been formerly known to be injurious to health. More recently, the dissolution of mercury from amalgam fillings has been causally linked to mercury poisoning according to several researchers. Also, it has been confirmed that dental amalgams come in contact with oral fluids during setting, such that the harmful mercury leaches and accumulate in various organs of the body. Mercury from the oval cavity passes through the cells and into the blood. Because of its high solubility in the lipoids, mercury will dispense readily to the brain, liver and kidneys with a half-life of more than 40 days.

Tests conducted on individuals with amalgam fillings revealed that the level of mercury present in the gases of expiration exceeded the permitted level in many of the cases investigated. It has been reported that the level of mercury concentration in the oral cavity increases with brushing of the teeth. Also, chewing chewing-gum reportedly gave rise to a substantial increase in the mercury content. The physiological symptoms associated with low-level exposure to toxic mercury include headaches, tiredness, loss of memory and other mental disturbances. Higher exposures result in more serious injury, such as cardiac problems and neurological ailments.

SUMMARY OF THE INVENTION

It is accordingly a primary object of the present invention to provide a method for neutralizing the harmful effects of mercury derived from amalgam fillings.

It is another primary objective of this invention to provide a substance which is capable of binding mercury to amalgam surfaces so as to prevent mercury from being released and mixing with oral fluids.

It has now been found that sulfur is effective in suppressing the toxicity of leaching mercury from dental amalgams. While sulfur is not a transitional metal, since mercury is normally found in the stable form of mercuric sulfide (HgS), it has been determined that sulfur provides an excellent material for binding mercury thereto and acts to inhibit mercury from passing into the body. Besides being antagonistic to the toxity of the mercury leaching in the oral fluids, the most unique effect that sulfur possesses is that it ensures that no harmful substances remain in the oral cavity or enter the body.

Thus, in one aspect of the present invention, a method is provided for preventing mercury released from amalgam fillings from passing into and adversely effecting the body which comprises applying an effective amount of sulfur to the hardened surfaces of existing amalgam dental fillings. The present method obviates the need of replacing old amalgam dental fillings in patients who suffer ailments resulting from the emission of mercury from such fillings. Sulfur can be used safely to form on the surfaces of amalgam fillings a protective layer which will prevent further dissolution of mercury.

In accordance with an alternative embodiment of the present invention, a method is provided for preparing the surface of dental cavities so that the dental amalgam which is used to fill the cavity exhibits a substantially reduced tendency to deteriorate over long periods of time. The method involved the application of a liner of sulfur to the cavity surfaces prior to filling the cavity with dental amalgam. Mercury diffuses from the amalgam into the sulfur lining during setting so that a Hg-S alloy region is formed between the amalgam and cavity surfaces. By this particular method, the deleterious effects of free mercury in the oral cavity can be eliminated while forming dental restorations. Investigations suggest that the mercury-sulfur region forms a stable protective barrier at the tooth-restoration interface which will prevent further dissolution of mercury. Dental restorations prepared in this manner are characterized by a continuous structural integrity and are expected to possess longer effective lifetimes than conventional dental amalgams.

The foregoing and other features, advantages and objects of the invention may be more fully appreciated by reference to the following detailed description.

DETAILED DESCRIPTION OF THE PREFERRED EMBODIMENTS

The bonding of sulfur to dental restoration surfaces may be achieved in accordance with one aspect of the present invention by applying an effective amount of sulfur to the restored surfaces of amalgam fillings. The sulfur may be applied in powder or liquid form in amounts sufficient to eliminate any free or unassociated mercury from the oral cavity. Generally, sulfur powder can be applied in a powder to free mercury ratio of at least 1:1, and preferably more on the order of 3:1. There is no upper limit as to how much sulfur powder can be safely used since there is no risk of sulfur being administered in an overdose. Thus, one can apply as much powder as is tolerable or economically feasible. A wetted swab or small brush may be conveniently used to periodically coat the restored tooth with sulfur powder. After brushing or swabbing for one to three minutes, the sulfur is removed from the mouth by rinsing with water.

Since most people regularly brush their teeth, the introduction of the sulfur bonding material into commercial toothpastes is considered the most suitable means for regularly treating amalgam fillings in accordance with this particular embodiment of the invention. The sulfur may be added in safe excess amounts and the toothpastes can contain as much as about 5% by weight sulfur, based on the total weight of the toothpaste composition. The teeth are cleaned in the normal manner with the toothpaste containing the sulfur and the foam generated is rinsed away from the mouth.

A protective coating comprising a thin layer of mercury sulfide (HgS) was found to be produced on the amalgam surfaces after regular brushing with the sulfur-containing toothpaste over the course of several weeks. This surface layer of HgS results in amalgams having improved mechanical properties such as increased compressive strengths and greater wear resistance. Also, no trace of unassociated mercury could be found upon analysis of the oral cavity subsequent to rinsing the amalgam surfaces treated in accordance this invention.

Although the protective layer of the present invention is most effectively applied in conjunction with brushing of the teeth, it is contemplated that sulfur may also be incorporated in commercial mouthwashes and the oral cavity treated in the manner normal with dental hygiene. In principle, the mouthwashes may contain up to about 5% by weight sulfur, based on the total weight of the mouthwash composition.

In accordance with an alternative method contemplated by the present invention, a liner of sulfur can be applied to a cavity surface prior to filling the cavity with dental amalgam. The sulfur liner can be deposited on the surfaces of the cavity in the form of a powder, paste or slurry which is sufficiently thin to provide a homogeneous coating on the cavity. Preferably, sulfur powder is mixed with a dental adhesive to form an adhesive-sulfur lining composition comprising about 50% to 75% by weight sulfur. Suitable dental adhesives must meet FDA and ADA specifications and include such materials as polyacrylate cements, silicate or phosphate cements, and the like.

The surfaces of the tooth cavity may best be coated with the sulfur-adhesive composition by application with a small brush, for example, and the dental amalgam is then inserted into the lined cavity by standard dental restoration procedures. The basic composition of the amalgams used are conventional and can contain Hg, Sn and Ag, with small amounts of Cu and Zn. Usually, the Hg is present in the amalgam in an amount of from about 45% to about 60% by weight before insertion. When the amalgam is packed into the lined cavity, free mercury will quickly diffuse into the sulfur-adhesive liner to form an essentially sulfur-mercury zone adjacent the cavity surfaces which is free of tin atoms. An integral restoration is subsequently formed by amalgamation which exhibits substantial resistant to corrosion. Also, it is believed that the sulfur lining material may promote adhesion between the applied dental restoration and the cavity surfaces.

It is also with the contemplation of the present invention to provide a setting composition for dental purposes comprising a dental amalgam alloy composed mainly of Ag and Sn and one or more of Au, Cu, Zn and Pd; Hg in an amount sufficient to amalgamate said alloy; and S. The amount of sulfur powder contained in the amalgam composition according to the present embodiment is about 0.05 to 5% relative to the total weigh of the alloy and the mercury to amalgamate it.

It should be understood that there may be various changes and modifications of the representative embodiments herein chosen for purposes of description without departing from the spirit and scope of the invention. Accordingly, the foregoing descriptions are not to be interpreted as restrictive of the invention beyond that necessitated by the following claims.

I claim:

1. A method for preventing mercury released from amalgam dental fillings from passing into and adversely effecting the body which comprises applying an effective amount of sulfur to surfaces of said amalgam dental fillings.

2. The method according to claim 1 wherein a mercury sulfide protective layer is formed over the amalgam surfaces.

3. The method according to claim 2 wherein said mercury sulfide protective layer is formed over the amalgam surfaces by brushing a tooth surface with a toothpaste composition containing an effective amount of sulfur.

4. The method according to claim 3 wherein said toothpaste composition contains up to about 5% by weight sulfur, based on the total weight of the toothpaste composition.

5. A method for forming dental restorations which comprises:
   preparing a cavity within a carious tooth for receiving a dental amalgam filling;
   coating the surfaces of said cavity with a layer of sulfur lining composition; and
   filling said cavity with a Ag-Hg-Sn dental amalgam, whereby free mercury present in said amalgam is diffused into and amalgamates with said sulfur of the lining composition so as to form an integral restoration which is substantially resistant to corrosion.

6. The method of claim 5 wherein said sulfur lining composition comprises a dental adhesive mixed with 50% to 75% by weight of sulfur.

* * * * *